United States Patent [19]

Mita et al.

[11] Patent Number: 4,918,216

[45] Date of Patent: Apr. 17, 1990

[54] PREPARATION PROCESS OF α-L-ASPARTYL-L-PHENYL-ALANINE METHYL ESTER OR HYDROHALIDE THEREOF

[75] Inventors: Ryuichi Mita; Toshio Katoh, both of Kawasaki; Chojiro Higuchi, Kamakura; Takeshi Oura, Zushi; Akihiro Yamaguchi, Kamakura, all of Japan

[73] Assignee: Mitsui Toatsu Chemicals, Incorporated, Tokyo, Japan

[21] Appl. No.: 357,618

[22] Filed: May 25, 1989

Related U.S. Application Data

[63] Continuation of Ser. No. 126,729, Nov. 30, 1987, abandoned.

[30] Foreign Application Priority Data

Dec. 5, 1986 [JP] Japan ................ 61-288888
Dec. 5, 1986 [JP] Japan ................ 61-288889

[51] Int. Cl.$^4$ ........................... C07C 101/02
[52] U.S. Cl. ........................... 560/41
[58] Field of Search ........................... 560/41

[56] References Cited

U.S. PATENT DOCUMENTS

| | | | |
|---|---|---|---|
| 3,833,553 | 9/1974 | Ariyoshi et al. | 260/112.5 |
| 3,879,372 | 4/1975 | Boesten | 260/112.5 |
| 3,933,781 | 1/1976 | Bachman et al. | 260/112.5 |
| 3,962,207 | 6/1976 | Uchiyama et al. | 260/112.5 |
| 4,021,418 | 5/1977 | Takemoto et al. | 260/112.5 |
| 4,071,511 | 1/1978 | Takemoto et al. | 260/112.5 |
| 4,088,649 | 5/1978 | Smith | 544/385 |
| 4,153,737 | 5/1979 | Berg et al. | 426/548 |
| 4,173,562 | 11/1979 | Bachman et al. | 260/112.5 |
| 4,333,872 | 6/1982 | Sampathkumar et al. | 260/112.5 |
| 4,634,790 | 1/1987 | Shinohara et al. | 560/40 |
| 4,740,616 | 4/1988 | Takemoto et al. | 562/448 |
| 4,801,732 | 1/1989 | Mita et al. | 560/40 |

FOREIGN PATENT DOCUMENTS

| | | |
|---|---|---|
| 0092933 | 11/1983 | European Pat. Off. |
| 0127411 | 12/1984 | European Pat. Off. |
| 0200311 | 12/1986 | European Pat. Off. .............. 560/41 |
| 2559773 | 2/1985 | France . |
| 46-1370 | 9/1971 | Japan . |
| 48-96557 | 12/1973 | Japan . |
| 51-113841 | 7/1976 | Japan . |
| 51-40069 | 11/1976 | Japan . |
| 53-82752 | 7/1978 | Japan . |
| 58-185545 | 10/1983 | Japan . |
| 59-130846 | 7/1984 | Japan . |
| 59-219258 | 12/1984 | Japan . |
| 59-225152 | 12/1984 | Japan . |
| 59-225153 | 12/1984 | Japan . |
| 60-50200 | 3/1985 | Japan . |
| 60-174799 | 9/1985 | Japan . |
| 61-218597 | 9/1986 | Japan .................... 560/41 |
| 1359123 | 7/1974 | United Kingdom . |
| 1464140 | 2/1977 | United Kingdom . |
| 2133409 | 7/1984 | United Kingdom . |

OTHER PUBLICATIONS

Chemical Abstracts, 80, 452, 96371X (1974).
Chemical Abstracts, 98019w, vol. 78, No. 15.
Chemical Abstracts, 105:153551s (1986).
World Patent Index (English Language Abstract of Japanese 60–174799).

*Primary Examiner*—Bruce D. Gray
*Attorney, Agent, or Firm*—Fisher, Christen & Sabol

[57] ABSTRACT

α-L-aspartyl-L-phenylalanine methyl ester or the hydrohalide thereof is prepared by esterifying α-L-aspartyl-L-phenylalanine or α-L-aspartyl-L-phenylalanine which has been formed in situ by treating an N-protected-α-L-aspartyl-L-phenylalanine in an aqueous solution of sulfuric acid or a methanol-containing aqueous solution of sulfuric acid in the presence of an alkali metal halide or alkaline earth metal halide in a medium composed of sulfuric acid, water and methanol, thereby to allow the resulting α-L-aspartyl-L-phenyl-alanine methyl ester to precipitate as its corresponding hydrohalide, and then isolating the hydrohalide; and when the preparation of the methyl ester is desired, neutralizing the hydrohalide.

23 Claims, No Drawings

PREPARATION PROCESS OF α-L-ASPARTYL-L-PHENYL-ALANINE METHYL ESTER OR HYDROHALIDE THEREOF

This application is a continuation of prior U.S. application Ser. No. 126,729 filing date Nov. 30, 1987, which is now abandoned.

BACKGROUND OF THE INVENTION (a) Field of the Invention

This invention relates to a novel and improved preparation process of α-L-aspartyl-L-phenylalanine methyl ester (hereinafter abbreviated as "α-APM") or a hydrohalide thereof.

(b) Description of the Related Art

Regarding the preparation of α-APM which is a substance useful as a sweetening agent and is recently in a growing demand for its strong sweet taste and sweetness characteristics for good quality, a number of processes have already been disclosed centering on chemical preparation processes. Among these, processes making use of an N-protected-L-aspartic anhydride as a carboxylic acid-activated derivative of L-aspartic acid are dominant. In particular, it is considered to be most advantageous industrially to prepare α-APM by using N-formyl-L-aspartic anhydride which can be obtained easily in a single step by reacting L-aspartic acid with formic acid and acetic anhydride, because the starting materials can be prepared easily and economically and the preparation process is relatively simple.

The above preparation processes of α-APM, which employs N-formyl-L-aspartic anhydride, features the use of L-phenylalanine methyl ester as the other starting material as disclosed typically in Japanese Patent Laid-Open No. 1350/1971. After formation of N-formyl-α-L-aspartyl-L-phenylalanine methyl ester as an intermediate, the formyl group as a protecting group is removed to provide α-APM. A variety of techniques has been proposed centering on the condensation reaction between N-formyl-L-aspartic anhydride and L-phenylalanine methyl ester, the inhibition of isomers, and the removal of the formyl group.

The processes making use of L-phenylalanine methyl ester as one of starting materials however involve cumbersome procedures in esterifying L-phenylalanine into L-phenylalanine methyl ester so as to carry out the condensation reaction with N-formyl-L-aspartic anhydride. Besides, it has also come to the surface as a result of the present inventors' finding that L-phenylalanine methyl ester is, in a free form, prone to undergo self-condensation and cyclization into 2,5-dibenzyl-3,6-dioxopiperazine. This tendency causes various industrial troubles such as yield reduction and quality deterioration of α-APM.

As a process for the preparation of α-APM which makes use of N-formyl-L-aspartic anhydride, it has hence been desired to develop a technique not using L-phenylalanine methyl ester as the other starting material.

As preparation processes not relying upon L-phenylalanine methyl ester, it has been disclosed that α-APM is prepared by subjecting N-formyl-L-aspartic anhydride to direct condensation with L-phenylalanine in acetic acid to form N-formyl-α-L-aspartyl-L-phenylalanine, removing the formyl group to obtain α-aspartyl-L-phenylalanine, and then esterifying the α-aspartyl-L-phenylalanine in the presence of hydrogen chloride in methanol (Japanese Patent Publication No. 26133/1980); and as an improvement to the esterification, α-L-aspartyl-L-phenylalanine is brought into contact with a medium composed of hydrogen chloride, methanol and water to esterify same, followed by crystallization of the resulting α-APM as its hydrochloride in a solid form (Japanese Patent Publication No. 50200/1985).

The former process is however accompanied by a drawback that the esterification reaction does not have high selectivity with respect to the two carboxylic acid groups, an esterification reaction of the β-carboxylic acid group and/or another esterification reaction of both α- and β-carboxylic acid groups take place to substantial extents in addition to the intended esterification of the α-carboxylic acid group and the selectivity to α-APM is hence reduced. On the other hand, the latter process has made it possible to improve the selectivity to α-APM by conducting the esterification reaction in an aqueous solution of hydrochloric acid so as to have the resultant α-APM to crystallized out as its hydrochloride outside the system. However, the isolation yield of α-APM is still as low as 50–60% (based on α-L-aspartyl-L-phenylalanine). The latter process is therefore not considered to be satisfactory fully in yield.

SUMMARY OF THE INVENTION

An object of this invention is to provide a process which can prepare α-APM with a high selectivity and in a high yield from α-L-aspartyl-L-phenylalanine or an N-protected-α-L-aspartyl-L-phenylalanine under mild conditions.

Other objects of this invention will become apparent from the following description.

The above and other objects of the present invention are achieved by the following preparation process of α-APM according to the invention:

A process for the preparation of α-L-aspartyl-L-phenylalanine methyl ester or the hydrohalide thereof, which comprises esterifying α-L-aspartyl-L-phenylalanine or α-L-aspartyl-L-phenylalanine which has been formed in situ by treating an N-protected-α-L-aspartyl-L-phenylalanine in an aqueous solution of sulfuric acid or a methanol-containing aqueous solution of sulfuric acid in the presence of an alkali metal halide or alkaline earth metal halide in a medium composed of sulfuric acid, water and methanol, thereby to allow the resulting α-L-aspartyl-L-phenylalanine methyl ester to precipitate as its corresponding hydrohalide, and then isolating the hydrohalide; and when the preparation of the methyl ester is desired, neutralizing the hydrohalide.

The process of this invention has numerous advantages. For example, the esterification reaction of α-L-aspartyl-L-phenylalanine is allowed to proceed under mild conditions. The use of the alkali metal halide or alkaline earth metal halide, in particular, magnesium chloride permits preparation of α-APM with a high selectively and in a high yield. Since the resulting α-APM crystallizes out as its hydrohalide, α-APM hydrohalide of good quality can be obtained by merely conducting filtration subsequent to the reaction. The reaction and separation procedures are simple. In addition, the starting material, i.e., α-L-aspartyl-L-phenylalanine or the N-protected-α-L-aspartyl-L-phenylalanine can be obtained by using L-phenylalanine as is without relying upon L-phenylalanine methyl ester the stability of which is poor in a solution, so that the the overall process has been simplified. The present preparation process of α-APM has a high industrial value.

DETAILED DESCRIPTION OF THE INVENTION

In the esterification of α-L-aspartyl-L-phenylalanine with methanol in an acidic medium, there are inherently formed, besides α-APM, α-L-aspartyl-L-phenylalanine β-methyl ester in which the β-carboxylic acid group of α-L-aspartyl-L-phenylalanine has been esterified as well as α-L-aspartyl-L-phenylalanine dimethyl ester in which the two carboxylic acid groups have been both esterified.

The reactions forming these three kinds of esterification products from the starting materials are equilibrium reactions. It is hence necessary to remove from the reaction system α-APM alone selectively out of the esterification products in order to increase the selectivity to the intended α-APM. It has hence been considered to result in an improvement to the selectivity to α-APM provided that the concentration of α-APM dissolved in the reaction solution can be reduced.

Following the above approach, the present inventors conducted an extensive investigation with a view toward preparing α-APM efficiently by esterifying α-L-aspartyl-L-phenylalanine in an aqueous solution of sulfuric acid although such an esterification had scarcely been practised previously. However, the resultant α-APM did not crystallize out as its sulfate in dilute sulfuric acid. The present inventors have hence proceeded with further work to investigate effects which would be available by the addition of various inorganic salts. In the course of the further work, it has been found surprisingly that the resulting α-APM crystallizes out selectively not as its sulfate but as its hydrohalide and moreover in a high yield when the esterification reaction is carried out in the presence of a certain metal halide, i.e., an alkali metal halide or alkaline earth metal halide.

Such a phenomenon has been neither known nor expected at all to date. Moreover, such a phenomenon does not take place no matter which halide other than alkali metal halides and alkaline earth methal halides is used. When other inorganic salts were used, crystallization was not observed even in the sulfate form.

The starting material is α-L-aspartyl-L-phenylalanine in the present invention. α-L-aspartyl-L-phenylalanine can be prepared by deprotecting an N-protected-α-L-aspartyl-L-phenylalanine, which has been obtained by the condensation of the corresponding N-protected-L-aspartic anhydride and L-phenylalanine, by a method known per se in the art. Here, formyl group, t-butoxycarbonyl group and the like may be mentioned as protecting groups. Formyl group is a particularly preferable protecting group from the viewpoint of the preparation of the starting material.

The starting material, α-L-aspartyl-L-phenylalanine, is not necessarily required to have a high purity. Inclusion of β-L-aspartyl-L-phenylalanine, which has been derived from the β-isomer byproduced upon condensation of N-formyl-α-L-aspartic anhydride with L-phenylalanine, phenyl alanine, aspartic acid or the like does not cause any particular problem so long as its content is at a level not adversely affecting the crystallization of an α-APM hydrohalide to be formed. In particular, the inclusion of β-L-aspartyl-L-phenylalanine in any amount up to about 30% does not impair the crystallization of the α-APM hydrohalide and moreover does not cause compounds derived from the β-isomer to crystallize out, whereby the quality of the α-APM hydrohalide to be isolated will not be deteriorated.

In the process of this invention, it is essential to esterify α-L-aspartyl-L-phenylalanine in the presence of an alkali metal halide or alkaline earth metal halide in a medium composed of sulfuric acid, water and methanol so that α-APM is caused to crystallize out in the form of a hydrohalide thereof.

The composition of the reaction medium is an important factor for the crystallization of the resulting α-APM as a solid hydrohalide thereof. The concentration of sulfuric acid may preferably be 5–50 wt. % with 8–40 wt. % being more preferred, said concentration being defined as sulfuric acid/(sulfuric acid + water)×100. On the other hand, the concentration of methanol may preferably be 3–35 wt. % with 5–30 wt. % being more preferred, said concentration being defined as methanol/(methanol + water)×100. Preferably, sulfuric acid and methanol may each be used in an amount of at least 1 equivalent relative to the starting material, i.e., α-L-aspartyl-L-phenylalanine.

The esterification reaction is carried out in the presence of an alkali metal halide or alkaline earth metal halide, preferably, an alkali metal chloride or alkaline earth metal chloride, specifically, lithium chloride, sodium chloride, potassium chloride, rubidium chloride, cesium chloride, beryllium chloride, magnesium chloride, calcium chloride, strontium chloride, barium chloride or the like. Among these metal chlorides, magnesium chloride is preferred especially. α-APM can be obtained in a still higher yield when magnesium chloride is used. This seems to indicate that the process of the present is not based on a mere acid-salt interchange reaction but metal cations take part in one way or another in the reaction.

Upon using the alkali metal halide or alkaline earth metal halide (hereinafter called "metal halide" collectively for the sake of brevity), it is not absolutely necessary to dissolve it completely in the above-described reaction medium. It may also be used in a suspended state. It may be feasible to use two or more of these metal halides in combination, although they are used singly in general.

The metal halide may be used in an amount of at least 1 equivalent, preferably, at least 1.1 equivalents relative to α-L-aspartyl-L-phenylalanine. Although the reaction still proceeds at a lower metal halide level, the selectivity to α-APM drops. It is hence not preferred to use the metal halide at such a low level. On the other hand, no particular limitation is imposed on the upper limit of the metal halide to be used. It is however not preferable to use it too much. Use of the metal halide in an excessive amount may complicate the separation of α-APM and the metal halide in some instances. Therefore, it is generally used in an amount of 20 equivalents or less relative to α-L-aspartyl-L-phenylalanine.

In the process of the present invention, there is no particular limitation imposed on the order of charging of the starting material, reaction medium and metal halide. By way of example, the raw material, i.e., α-L-aspartyl-L-phenylalanine and metal halide are charged into a reaction vessel, in which a medium composed of sulfuric acid, water and methanol in predetermined amounts has been charged in advance. Thereafter, the esterification reaction is carried out at a predetermined temperature.

The temperature of the esterification reaction may be 0°–60° C., preferably, 10°–50° C. Any unduly low reaction temperatures slow down the esterification reaction. If the temperature is raised excessively, the cleavage of peptide bonds is promoted and at the same, the solubility of α-APM hydrohalide is increased. As a result, the yield of α-APM is reduced. It is hence not preferable to conduct the esterification reaction at any unduly low or excessively high temperatures.

In the process of this invention, the resulting α-APM is allowed to crystallize out successively as its hydrohalide from the reaction system. After the reaction and subsequent optional cooling, α-APM is therefore isolated as its hydrohalide by centrifugation, filtration or the like.

In the present invention, α-L-aspartyl-L-phenylalanine which has been formed after removing the protecting group by treating the N-protected-α-L-aspartyl-L-phenylalanine in the aqueous solution of sulfuric acid or the methanol-containing aqueous solution of sulfuric acid may also be used directly as a starting material for the esterification without its isolation.

The protecting group of the N-protected-α-L-aspartyl-L-phenylalanine, the starting material for the above process, is supposed to be removable rather easily by acid hydrolysis. Specifically, formyl group, t-butoxycarbonyl group or the like may be mentioned. Formyl group is particularly suitable when the preparation of the starting material is taken into parallel consideration.

As a preparation process of N-formyl-α-L-aspartyl-L-phenylalanine, it may be prepared in a good yield by a process developed previously by the present inventors, namely, by condensing N-formyl-L-aspartic anhydride and L-phenylalanine in water and then causing the condensation product to crystallize out around pH 3. It is not absolutely essential for this N-formyl-α-L-aspartyl-L-phenylalanine to have a high degree of purity. Inclusion of the β-isomer, namely, N-formyl-β-aspartyl-L-phenylalanine and in some instances, L-phenylalanine, (N-formyl)-L-aspartic acid does not cause any particular problem so long as their contents are at levels not adversely affecting the crystallization of an α-APM hydrohalide to be formed. In particular, the inclusion of N-formyl-β-L-aspartyl-L-phenylalanine in any amount up to about 30% does not impair the crystallization of the α-APM hydrohalide and moreover does not cause compounds derived from the β-isomer to crystallize out, whereby the quality of the α-APM hydrohalide to be isolated will not be deteriorated.

The above-described process making use of N-formyl-α-L-aspartyl-L-phenylalanine as the starting material comprises a step in which the formyl group is removed and another step in which α-L-aspartyl-L-phenylalanine formed by the removal of the formyl group is esterified. First of all, the removal step of the formyl group, which is carried out prior to the esterification, is effected in an aqueous solution of sulfuric acid or a methanol-containing aqueous solution of sulfuric acid. In a specific embodiment, this step is carried out by charging N-formyl-α-L-aspartyl-L-phenylalanine into an aqueous solution or methanol-containing aqueous solution containing sulfuric acid in an amount at least 1 equivalent relative to the N-formyl-α-L-aspartyl-L-phenylalanine and then heating the reaction mixture under stirring for a predetermined period of time. The aqueous solution of sulfuric acid is used in a range of about 3–70 wt. % in terms of concentration defined by sulfuric acid/(sulfuric acid + water) × 100. Where methanol is contained, there is no particular limitation to the amount of methanol to be used. Taking into consideration the amount of methanol to be used in the subsequent esterification step, it is however preferable to use it in an amount not exceeding the amount to be used in the esterification step. It is of course possible to effect the removal of the formyl group in the presence of methanol in an amount greater than the amount to be used in the subsequent esterification step. However, this requires an extra procedure for the recovery of methanol by concentration in the subsequent esterification step. Use of methanol in such a large amount is therefore not considered to be preferable in view of the efficiency of work.

The reaction temperature of the step in which the formyl group is removed may range from 30° C. to 70° C., preferably, 40° C.–60° C. If the reaction temperature is too low, it takes unduly long period of time for the removal of the formyl group. If the temperature is too high on the contrary, side reactions such as cleavage of peptide bonds tend to occur easily. The reaction time varies depending on the concentration of sulfuric acid, its amount to be used, the reaction temperature, etc. and cannot be specified sweepingly. However, it is usually conducted in a period ranging from 0.5 hour to 20 hours. The formyl group is removed by the above procedure from N-formyl-α-L-aspartyl-L-phenylalanine so that α-L-aspartyl-L-phenylalanine is formed. Needless to say, when the removal of the formyl group is effected in a methanol-containing aqueous solution of sulfuric acid, not only deformylation but also an esterification reaction are induced although the degree of the latter reaction varies depending on the reaction conditions. α-L-aspartyl-L-phenylalanine formed in the first step is in a state dissolved in the reaction mixture. The thus-formed α-L-aspartyl-L-phenylalanine is subjected to the next esterification step without isolation.

α-L-aspartyl-L-phenylalanine, which has been obtained in the above manner and may contain its ester in some instance, is then esterified in the presence of the metal halide in a medium composed of sulfuric acid, water and methanol, whereby it is converted into an α-APM hydrohalide.

The concentration and amount of sulfuric acid and methanol and the kind of the metal halide in the esterification step are the same as the above-described conditions for the preparation of an α-APM hydrohalide from α-L-aspartyl-L-phenylalanine as a starting material. Namely, the concentration of sulfuric acid may preferably be 5–50 wt. % with 8–40 wt. % being more preferred, said concentration being defined as sulfuric acid/(sulfuric acid + water) × 100. On the other hand, the concentration of methanol may preferably be 3–35 wt. % with 5–30 wt. % being more preferred, said concentration being defined as methanol/(methanol + water) × 100. Preferably, sulfuric acid and methanol may each be used in an amount of at least 1 equivalent relative to the starting material, i.e., N-formyl-α-L-aspartyl-L-phenylalanine. Preferred as the metal halide is a metal chloride, specifically, lithium chloride, sodium chloride, potassium chloride, rubidium chloride, cesium chloride, beryllium chloride, magnesium chloride, calcium chloride, strontium chloride, barium chloride or the like. Magnesium chloride is particularly preferred. Such a metal halide may be used in an amount of at least 1 equivalent, preferably, at least 1.1 equivalents relative to the N-formyl-α-L-aspartyl-L-phenylalanine.

In a specific embodiment, the esterification step may be carried out by cooling as an optional procedure the reaction mixture, which has been obtained in the preceding step, namely, the removal step of the formyl group, charging sulfuric acid, water, methanol and metal halide to their predetermined concentrations or in their predetermined amounts and then conducting the esterification reaction.

The reaction temperature of the esterification may range from 0° C. to 60° C., with 10° C.–50° C. being preferred.

α-APM formed by the above esterification reaction crystallizes out as its hydrohalide successively from the reaction system. After the reaction and subsequent optional cooling, α-APM is therefore isolated as its hydrohalide by centrifugation, filtration or the like.

The thus-isolated α-APM hydrohalide may be converted into free α-APM by neutralizing same with a caustic alkali, alkali carbonate or alkali bicarbonate in an aqueous medium by a method known per se in the art.

The present invention will hereinafter be described in detail by the following Examples.

EXAMPLE 1

α-L-aspartyl-L-phenylalanine (14.0 g) was added to and dissolved in a medium which was composed of 9.6 g of methanol, 21.2 g of concentrated sulfuric acid and 44.4 g of water. Magnesium chloride hexahydrate (30.5 g) was then added to the resultant solution, followed by an esterification reaction at 20°–25° C. After proceeding with the reaction for 3 days, crystals precipitated were collected by filtration and then washed with chilled water. The weight of a wet cake thus obtained was 20.3 g. As a result of an analysis of the wet cake by high-performance liquid chromatography, the content of α-APM (as converted into its free form) was found to be 12.0 g (yield: 81.6% based on α-L-aspartyl-L-phenylalanine).

A portion of the crystals thus obtained was dissolved in water, followed by an addition of an aqueous solution of barium chloride. Precipitation was hardly observed. The solution was however turned cloudy with an aqueous solution of silver nitrate. The wet cake was recrystallized for purification from water and resultant crystals were dried. As a result of an elemental analysis on a sample of the thus-dried crystals, the crystals were confirmed to be α-APM.HCl dihydrate.

Elemental analysis data (%): Calculated for $C_{14}H_{23}N_2O_7Cl$: C, 45.84; H, 6.32; N, 7.64; Cl, 9.67. Found: C, 45.68; H. 6.45; N, 7.60; Cl, 9.74.

EXAMPLE 2:

Anhydrous magnesium chloride (19.0 g) was added to in a medium which was composed of 25.5 g of concentrated sulfuric acid, 72.5 g of water and 8 g of methanol. α-L-Aspartyl-L-phenylalanine (28.0 g) was then added to and dissolved in the solution, followed by a reaction at 30°–35° C. Upon an elapsed time of a certain period of time after the initiation of the reaction, α-APM hydrochloride started crystallizing out. After proceeding with the reaction for 2 days at the same temperature, the reaction mixture was cooled to 20° C. Crystals thus precipitated were collected by filtration and then washed with chilled water, thereby obtaining a wet α-APM.HCl cake containing 24.6 g of free α-APM. Yield: 83% (based on α-L-aspartyl-L-phenylalanine).

The thus-obtained wet cake of α-APM hydrochloride was dissolved in 400 ml of water, to which a 20% aqueous solution of sodium carbonate was gradually added dropwise to neutralize the former solution. The resultant mixture was cooled to 5° C. and after stirring it for 30 minutes at the same temperature, the mixture was filtered. Crystals thus collected were washed with chilled water and then dried in vacuo to obtain free α-APM. Yield: 21.2 g. $[\alpha]_D^{20}$: 15.6 (c=4, 15N formic acid). As a result of an analysis by high-performance liquid chromatography, it was only α-APM that was detected. No impurities were detected.

COMPARATIVE EXAMPLE 1:

The procedures of Example 2 were followed except that 7.3 g of hydrogen chloride was used in place of magnesium chloride. After proceeding with the reaction at 30° C. for 2 days, the reaction mixture was analyzed by high-performance liquid chromatography. As a result, the yield of α-APM was found to be as low as 32% (based on α-L-aspartyl-L-phenylalanine).

EXAMPLE 3:

The procedures of Example 2 were followed except that the amount of methanol used and the reaction time and temperature were changed to 4.8 g and 3 days at 30° C. respectively. α-APM hydrochloride was obtained in an isolation yield of 76.3% (based on α-L-aspartyl-L-phenylalanine).

EXAMPLE 4:

The procedures of Example 2 were followed except that the amount of water was changed to 113.5 g and the reaction was conducted at 30°–35° C. for 4 days. α-APM hydrochloride was obtained in an isolation yield of 79.6%.

EXAMPLES 5–8:

α-APM hydrochloride was separately obtained by conducting a reaction in the same manner as in Example 1 except that in lieu of magnesium chloride, various other metal chlorides were used separately. Results are summarized in Table 1.

TABLE 1

| Ex. No. | Metal chloride | | Reaction (°C./days) | Isolation* yield of α-APM.HCl |
|---|---|---|---|---|
| | Kind | Amount used (g) | | |
| 5 | Lithium chloride | 12.7 | 20–25/4 | 72.3 |
| 6 | Potassium chloride | 14.9 | 30–35/4 | 69.4 |
| 7 | Beryllium chloride | 20.0 | 30–35/4 | 67.1 |
| 8 | Sodium chloride | 9.0 | 30–35/4 | 66.5 |

*Based on L-aspartyl-L-phenylalanine.

EXAMPLE 9:

Charged and dissolved in a medium composed of 30 g of concentrated sulfuric acid, 97.8 g of water and 9.6 g of methanol was 35.8 g of α-L-aspartyl-L-phenylalanine containing 22 wt. % of β-L-aspartyl-L-phenylalanine. After adding 23.3 g of anhydrous magnesium chloride into the resultant solution, the contents were reacted at 30°–35° C. for 4 days. The reaction mixture was thereafter cooled to 20° C. and crystals thus precipitated were collected by filtration. The crystals were washed with chilled water, thereby obtaining α-APM hydrochloride. As a result of an analysis by high-performance liquid chromatography, the hydrochloride was found to contain 23.4 g of α-APM (as converted into its free form). Yield: 79.6% (based on α-L-aspartyl-L-phenylalanine).

The thus-obtained cake scarcely contained β-L-aspartyl-L-phenylalanine and compounds derived therefrom.

EXAMPLE 10:

A medium composed of 21.2 g of concentrated sulfuric acid, 60.6 g of water and 9.6 g of methanol was heated to 50° C., followed by an addition of 15.4 g (0.05 mole) of N-formyl-α-L-aspartyl-L-phenylalanine at 50°–55° C. over 30 minutes. The reaction was conducted for further 2 hours to remove the formyl group.

The reaction mixture was cooled to 20° C., and 14.3 g of anhydrous magnesium chloride was added, followed by a reaction at 20°–25° C. for 4 days. As the reaction proceeded, crystals of α-APM hydrochloride precipitated little by little. After the reaction, the precipitated crystals were collected by filtration and washed with chilled water. Weight of the wet cake: 19.4 g. As a result of an analysis of the wet cake by high-performance liquid chromatography, the content of α-APM (as converted into its free form) was found to be 11.8 g. Yield: 80.2% (based on N-formyl-α-L-aspartyl-L-phenylalanine). A portion of the wet cake was recrystallized for purification from water and resultant crystals were dried in vacuo. Results of an elemental analysis on a sample of the thus-dried crystals were in conformity with those of α-APM.HCl dihydrate.

Elemental analysis data (%): Calculated for $C_{14}H_{23}N_2O_7Cl$: C, 45.84; H, 6.32; N, 7.64; Cl, 9.67. Found: C, 45.62; H. 6.54; N, 7.51; Cl, 9.68.

A portion of the sample was dissolved in a small amount of water, followed by an addition of an aqueous solution of barium chloride. The solution was however not clouded substantially. It was however turned cloudy with an aqueous solution of silver nitrate, thereby confirming that the sample was the hydrochloride.

EXAMPLE 11:

A medium composed of 25.5 g of concentrated sulfuric acid and 72.5 g of water was heated to 50° C., followed by a gradual addition of 30.8 g (0.1 mole) of N-formyl-α-L-aspartyl-L-phenylalanine over about 1 hour. The reaction was conducted for further 3 hours at 50°–60° C. to remove the formyl group, so that α-L-aspartyl-L-phenylalanine was formed. The reaction mixture was then cooled to 20° C., and 9.6 g of methanol and 18.7 g of anhydrous magnesium chloride were added. The reaction mixture was heated to 30° C., followed by a reaction at 30°–35° C. for 4 days. As the reaction proceeded, crystals of α-APM hydrochloride precipitated little by little. After the reaction, the reaction mixture was cooled to 20° C., and the precipitated crystals were collected by filtration and washed with chilled water to obtain a wet α-APM.HCl cake containing 23.9 g of α-APM (as converted into its free form). Yield: 81.4% (based on N-formyl-α-L-aspartyl-L-phenylalanine).

The thus-obtained α-APM hydrochloride was dissolved in 400 ml of water, followed by a dropwise addition of a 20% aqueous solution of sodium carbonate to raise the pH of the solution to 5.2. The solution was cooled to 5° C. and then filtered to collect crystals. After washing the crystals with chilled water, they were dried in vacuo. Yield: 20.6 g. $[\alpha]_D^{20}$: 15.8 (c=4, 15N formic acid).

COMPARATIVE EXAMPLE 2:

A reaction was carried out in the same manner as

TABLE 2

| Ex. No. | Metal chloride Kind | Amount used (g) | Reaction (°C./days) | Isolation* yield of α-APM.HCl |
| --- | --- | --- | --- | --- |
| 14 | Lithium chloride | 12.7 | 20–25/5 | 68.4 |
| 15 | Potassium chloride | 14.9 | 30–35/5 | 66.1 |
| 16 | Sodium chloride | 24.1 | 30–35/4 | 65.3 |

*Based on L-aspartyl-L-phenylalanine.

EXAMPLE 17:

Into a medium composed of 30 g of concentrated sulfuric acid, 97.8 g of water and 9.6 g of methanol, was charged at 50°–55° C. over about 30 minutes 38.5 g of N-formyl-α-L-aspartyl-L-phenylalanine containing 20 wt. % of N-formyl-β-L-aspartyl-L-phenylalanine, followed by a reaction at 50°–60° C. for additional 2 hours to remove the formyl group. The reaction mixture was then cooled and after an addition of 23.0 g of anhydrous magnesium chloride, the contents were reacted at 30°–35° C. for 6 days. The reaction mixture was cooled to 20° C. and crystals thus precipitated were collected by filtration to obtain α-APM hydrochloride. As a result of an analysis by high-performance liquid chromatography, the hydrochloride was found to contain 21.9 g of α-APM (as converted into its free form). Yield: 74.4% (based on N-formyl-α-L-aspartyl-L-phenylalanine). in Example 11 except for the use of 7.3 g of hydrogen chloride instead of magnesium chloride. Precipitation of α-APM hydrochloride as crystals was scarcely observed even when reacted at 30° C. for 2 days. As a result of an analysis of the reaction mixture by high-performance liquid chromatography, the yield of α-APM was found to be as low as 26% (based on N-formyl-α-L-aspartyl-L-phenylalanine).

EXAMPLE 12:

A medium composed of 25.5 g of concentrated sulfuric acid, 72.5 g of water and 4.8 g of methanol was heated to 50° C., followed by a gradual addition of 30.8 g (0.1 mole) of N-formyl-α-L-aspartyl-L-phenylalanine over about 30 minutes. Thereafter, the contents were reacted for 2 hours at 50°–55° C. to remove the formyl group. The thus-obtained reaction mixture was then cooled to 20° C. and after an addition of 16.8 g of anhydrous magnesium chloride, a reaction was conducted for 5 days at 30°–35° C. After the reaction, the reaction mixture was cooled to 20° C. and crystals thus precipitated were collected by filtration and then washed with chilled water to obtain a wet cake of α-APM hydrochloride.

As a result of an analysis by high-performance liquid chromatography, the wet cake was found to contain 22.1 g of α-APM (as converted into its free form). Yield: 75.1% (based on N-formyl-α-L-aspartyl-L-phenylalanine).

EXAMPLE 13:

A medium composed of 25.5 g of concentrated sulfuric acid, 113.5 g of water and 12.8 g of methanol was heated to 50° C., followed by a gradual addition of 30.8 g (0.1 mole) of N-formyl-α-L-aspartyl-L-phenylalanine over about 30 minutes. Thereafter, the contents were reacted for 2 hours at 50°–60° C. to remove the formyl group. The thus-obtained reaction mixture was then cooled to 20° C. and 28.0 g of anhydrous magnesium chloride was added, followed by a reaction at 30°–35° C. for 5 days. Crystals thus precipitated were collected by filtration and then washed with chilled water to obtain a wet α-APM.HCl cake containing 21.5 g of α-APM (as converted into its free form). Yield: 73.1% (based on N-formyl-α-L-aspartyl-L-phenylalanine).

EXAMPLES 14–16:

α-APM hydrochloride was separately obtained by conducting a reaction in the same manner as in Example 10 except that in lieu of anhydrous magnesium chloride, various other metal chlorides were used separately. Results are summarized in Table 2.

Incidentally, compounds derived from the β-isomer were scarcely contained in the thus-obtained cake.

What is claimed is:

1. A process for the preparation of the hydrohalide of α-L-aspartyl-L-phenylalanine methyl ester, comprising esterifying α-L-aspartyl-L-phenylalanine in the presence of an alkali metal halide or alkaline earth metal halide in a medium consisting of sulfuric acid, water and methanol, the amount of the alkali metal halide or alkaline earth metal halide being at least 1 equivalent relative to the α-L-aspartyl-L-phenylalanine, thereby allowing the resulting α-L-aspartyl-L-phenylalanine methyl ester to precipitae as its corresponding hydrohalide, and then isolating the hydrohalide.

2. The process as claimed in claim 1, wherein the concentration of the sulfuric acid is 5–50 wt. % based on the sum of the sulfuric acid and water in the reaction system, the concentration of the methanol is 3–35 wt. % based on the sum of the methanol and water in the reaction system, and the amounts of the sulfuric acid and methanol are each at least 1 equivalent relative to the α-L-aspartyl-L-phenylalanine.

3. The process as claimed in claim 1, wherein an alkali metal chloride or alkaline earth metal chloride is used.

4. The process as claimed in claim 1, wherein magnesium chloride is used.

5. The process as claimed in claim 1, wherein the esterification is conducted at 0°–60° C.

6. The process as claimed in claim 1, wherein the α-L-aspartyl-L-phenyl alanine is that formed in situ by treating an N-protected-α-L-aspartyl-L-phenylalanine in an aqueous solution of sulfuric acid or a methanol-containing aqueous solution of sulfuric acid.

7. The process as claimed in claim 6, wherein the concentration of the sulfuric acid is 5–50 wt. % based on the sum of the sulfuric acid and water in the reaction system, the concentration of the methanol is 3–35 wt. % based on the sum of the methanol and water in the reaction system, and the amounts of the sulfuric acid and methanol are each at least 1 equivalent relative to the N-protected-α-L-aspartyl-L-phenylalanine.

8. The process as claimed in claim 6, wherein an alkali metal chloride or alkaline earth metal chloride is used.

9. The process as claimed in claim 6, wherein magnesium chloride is used.

10. The process as claimed in claim 6, wherein the esterification is conducted at 0°–60° C.

11. A process for the preparation of α-L-aspartyl-L-phenylalanine methyl ester comprising esterifying α-L-aspartyl-L-phenylalanine in the presence of an alkali metal halide or alkaline earth metal halide in a medium composed of sulfuric acid, water and methanol, the amount of the alkali metal halide or alkaline earth metal halide being at least 1 equivalent relative to the α-L-aspartyl-L-phenylalanine, thereby to allow the resulting α-L-aspartyl-L-phenylalanine methyl ester to precipitate as its corresponding hydrohalide, then isolating the hydrohalide, and neutralizing the hydrohalide to provide the methyl ester.

12. The process as claimed in claim 11 wherein the concentration of the sulfuric acid is 5 to 50 weight percent based on the sum of the sulfuric acid and water in the reaction system, the concentration of the methanol is 3 to 35 weight percent based on the sum of the methanol and water in the reaction system, and the amounts of the sulfuric acid and methanol are each at least 1 equivalent relative to the α-L-aspartyl-L-phenylalanine.

13. The process as claimed in claim 11 wherein an alkali metal chloride or alkaline earth metal chloride is used.

14. The process as claimed in claim 11 wherein magnesium chloride is used.

15. The process as claimed in claim 11 wherein the esterification is conducted at 0° to 60° C.

16. The process as claimed in claim 1, wherein the α-L-aspartyl-L-phenylalanine is that formed in situ by treating an N-protected-α-L-aspartyl-L-phenylalanine in an aqueous solution of sulfuric acid or a methanol-containing aqueous solution of sulfuric acid.

17. The process as claimed in claim 16 wherein the concentration of the sulfuric acid is 5 to 50 weight percent based on the sum of the sulfuric acid and water in the reaction system, the concentration of the methanol is 3 to 35 weight percent based on the sum of the methanol and water in the reaction system, and the amounts of the sulfuric acid and methanol are each at least 1 equivalent relative to the N-protected-α-L-aspartyl-L-phenylalanine.

18. The process as claimed in claim 16 wherein an alkali metal chloride or alkaline earth metal chloride is used.

19. The process as claimed in claim 16 wherein magnesium chloride is used.

20. The process as claimed in claim 16 wherein the esterification is conducted at 0° to 60° C.

21. The process as claimed in claim 11 wherein the neutralization of the hydrohalide is conducted by contacting the hydrohalide with an aqueous solution of a base selected from the group consisting of a caustic alkali, an alkali carbonate and an alkali bicarbonate.

22. The process as claimed in claim 21 wherein the base is sodium carbonate.

23. The process as claimed in claim 21 wherein the neutralized aqueous mixture is cooled and the precipitate is filtered out of the neutralized aqueous mixture.

* * * * *